United States Patent
Marjamaki et al.

(10) Patent No.: US 7,140,266 B2
(45) Date of Patent: Nov. 28, 2006

(54) DEVICE FOR DETERMINING THE SIZE DISTRIBUTION OF AEROSOL PARTICLES

(75) Inventors: Marko Marjamaki, Tampere (FI); Mikko Moisio, Tampere (FI); Jorma Keskinen, Tampere (FI); Juha Tikkanen, Tampere (FI)

(73) Assignee: Dekati Oy, Tempare (FI)

( * ) Notice: Subject to any disclaimer, the term of this patent is extended or adjusted under 35 U.S.C. 154(b) by 0 days.

(21) Appl. No.: 10/363,385

(22) PCT Filed: Aug. 31, 2001

(86) PCT No.: PCT/FI01/00754

§ 371 (c)(1),
(2), (4) Date: Jul. 21, 2003

(87) PCT Pub. No.: WO02/18910

PCT Pub. Date: Mar. 7, 2002

(65) Prior Publication Data

US 2004/0025567 A1 Feb. 12, 2004

(30) Foreign Application Priority Data

Sep. 1, 2000  (FI) ................................. 20001930

(51) Int. Cl.
*G01N 15/02* (2006.01)
(52) U.S. Cl. .................. 73/865.5; 324/71.4; 73/863.22
(58) Field of Classification Search ............... 73/865.5, 73/863.22, 61.72, 64.56; 324/71.4
See application file for complete search history.

(56) References Cited

U.S. PATENT DOCUMENTS

| | | | |
|---|---|---|---|
| 4,837,440 A | 6/1989 | Burtscher et al. | |
| 5,654,205 A * | 8/1997 | Chae et al. | ................. 73/865.5 |
| 5,746,832 A | 5/1998 | Chae et al. | |
| 6,012,343 A | 1/2000 | Boulaud et al. | |
| 6,230,572 B1 * | 5/2001 | Pui et al. | ................. 73/863.21 |
| 6,401,553 B1 * | 6/2002 | Keskinen et al. | ......... 73/865.5 |
| 7,066,037 B1 * | 6/2006 | Keskinen et al. | ......... 73/865.5 |
| 2003/0082825 A1 * | 5/2003 | Lee et al. | .................. 436/148 |
| 2005/0119836 A1 * | 6/2005 | Keskinen et al. | ............ 702/23 |

FOREIGN PATENT DOCUMENTS

| | | |
|---|---|---|
| DE | 4429831 | 4/1995 |
| GB | 2344426 | 6/2000 |

OTHER PUBLICATIONS

SE Pratsinis, Aerosol measurements, ETH, pp. 1-4.*

* cited by examiner

*Primary Examiner*—Hezron Williams
*Assistant Examiner*—Nashmiya Fayyaz
(74) *Attorney, Agent, or Firm*—Venable LLP; Eric J. Franklin

(57) ABSTRACT

The invention relates to a device (30) for determining the size distribution of aerosol particles from a flow (11), the device (30) comprising an electric mobility analyzer (10) and an impactor (20), connected to each other in such a way that the nozzle part (22*a*) of the first stage of the impactor (20) is simultaneously the bottom plate of said mobility analyzer (10).

8 Claims, 2 Drawing Sheets

DEVICE FOR DETERMINING THE SIZE DISTRIBUTION OF AEROSOL PARTICLES

FIELD OF THE INVENTION

The invention relates to a device for determining the size distribution of aerosol particles.

BACKGROUND OF THE INVENTION

With tightening environmental regulations, there is an increasing need for real-time measurement of particle emissions. In particular, the need for measurement is present in the development of filtering methods, in the research of various combustion processes, as well as in monitoring processes for actual emissions. For classifying the mobility size distribution of aerosol particles, real-time aerosol measurements apply various analyzers which measure the electric mobility of particles, such as differential mobility analyzers (DMA).

FIG. 1 shows, in a simplified diagram, a mobility analyzer 10 according to prior art. The mobility analyzer 10 consists of an electrically conductive, preferably cylindrical frame part 12, which is coupled to a first constant potential, typically the ground plane, and thereby acts as an outer electrode. The ends of the frame part 12 are provided with cover and bottom plates 17a and 17b. An inner electrode 13 is placed centrally in the frame part 12 and coupled via a power supply 15 to a second constant potential. The power supply 15 is used to produce an electric field between the frame part 12 of the device and the inner electrode 13.

The cover and bottom plates 17a and 17b of the analyzer 10 are equipped with the necessary ducts to implement inlet and outlet pipes 18, 14 and 16 as well as the couplings required by the inner electrode 13.

So that particles could be separated on the basis of their electric mobility by means of the electric field, the aerosol particles to be introduced into the analyzer must have an electric charge before the analyzer 10. For this reason, the aerosol particles are typically charged by a separate charger (not shown in FIG. 1) before the analyzer 10. The flow 11 coming from the charger is led via the inlet pipe 18 to the analyzer. The flow 11 passes through the analyzer 10, primarily exiting via the outlet pipe 16.

When entering the electric field between the frame part of the analyzer 10 and the inner electrode 13, the charged aerosol particles in the flow 11 are drawn, depending on the sign of the charge, either towards the frame part 12 or towards the inner electrode 13. Typically, mobility analyzers are implemented in such a way that interesting aerosol particles are drawn towards the inner electrode 13.

The rate at which the aerosol particles drift towards the electrodes depends on the electric mobility of the particles, which is dependent, in a known manner, on e.g. the mass and charge of the particle.

Particles having greater electric mobility move faster towards the electrode determined by their charge, typically the inner electrode 13. As a result of this, the particles with greater electric mobility hit the inner electrode 13 sooner than particles with smaller electric mobility. As the flow 11 passes towards the bottom plate 17b of the analyzer 10, particles with greater electric mobility hit closer to the end of the inner electrode 13 on the side of the cover plate 17a, and particles with smaller mobility hit closer to the end of the inner electrode 13 on the side of the bottom plate 17b. Those particles whose electric mobility is so small that they do not reach the inner electrode 13 when moving with the flow 11 through the analyzer, are discharged via the outlet pipe 16 from the analyzer.

Depending on the solution to be used, the above-presented mobility analyzer 10 can be implemented by a number of different ways. In its simplest form, the solution does not apply the outlet pipe 14 placed inside the electrode 13 at all, wherein the complete flow 11 coming into the analyzer 10 is discharged through orifices in the bottom plate 17b into the outlet pipe 16. Thus, it is possible to use the analyzer to remove from the flow 11 the particles which have greater electric mobility than a certain value and which are deposited on the inner electrode 13.

DMA analyzers are typically implemented in such a way that the inner electrode 13 is provided with a narrow slit 19 which is coupled to the second outlet pipe 14. Thus, particles falling into the slit 19 are absorbed into the second outlet pipe 14. If the analyzer 10 is constructed in such a way that the flow 11 to be measured is introduced into the analyzer 10 at a certain distance from the inner electrode 13, the voltage difference between the frame part 12 of the analyzer 10 and the inner electrode 13 can be adjusted to determine the mobility range of the particles falling into the slit 19. Thus the DMA analyzer can be used to separate particles falling into a certain mobility range from the flow 11 under analysis, by guiding them into the second outlet pipe 14, wherein particles with greater electric mobility adhere to the inner electrode 13 before the slit 19 and particles with smaller mobility are discharged with the flow along the outlet pipe 16.

Furthermore, it is known to implement the mobility analyzer 10 as a multi-channel differential mobility analyzer, in which the inner electrode 13 of the mobility analyzer 10 is equipped with several detection surfaces which indicate the number of particles hitting them, for example on the basis of the charges transferred by the particles hitting them. The detection surfaces are preferably placed onto the surface of the inner electrode 13 in such a way that each of them collects particles falling into a certain mobility range. By monitoring the signals given by these detection surfaces, it is possible to measure, in real time, the electric mobility of particles in the flow 11 under analysis and, on the basis of this, to compute the size distribution based on the electric mobility diameter of the particles.

The mobility analyzers are most precise for particles with a small mass, because the electric mobility of the particles is inversely proportional to the mass of the particle; that is, the greater the mass of the particle, the smaller the mobility of the particle. In typical particle measurement environments, the aim is to measure particles whose diameters vary from some tens of nanometers to tens of micrometers. In this range, there are typically differences of several orders in the mobility of the particles, wherein it is extremely difficult to measure the whole range simultaneously by one device with a sufficiently high precision. Electric mobility analyzers are primarily used in fine particle analyses, in which the mobility analyzers are most precise, due to the high mobility of the fine particles.

For measuring primarily larger particles, classification methods based on the aerodynamic diameter of the particles are normally used, such as impactors. The electrical low pressure impactor (ELPI) developed by Dekati Ltd provides a solution for real-time measurement of aerosol particles.

FIG. 2 shows a cross-sectional view of two upper stages 21a and 21b of an electrical low pressure impactor 20, and chambers 29a and 29b related to them. An air flow 11 to be analyzed is sucked by means of an underpressure produced by a pump (not shown in FIG. 2) into the electrical low pressure impactor 20 and into the first chamber 29a of the impactor. Each stage comprises a nozzle part 22a, 22b, equipped with orifices, through which the air flow 11 carrying particles flows. Collection surfaces 23a, 23b are placed behind the nozzle parts 22a, 22b. Each collection surface 23a, 23b is equipped with at least one outlet 25, through which the flow 11 is allowed to flow to the next chamber or out of the impactor. Insulators 24a, 24b, 24c placed between the stages 20a, 20b insulate the different stages 20a, 20b from each other and the first stage of the impactor from the cover part 26.

The direction of the air flow 11 flowing from the orifices of the nozzle part 22a, 22b is abruptly changed when it meets the collection surface 23a, 23b. The particles carried by the flow 11 and having a sufficiently large aerodynamic particle size cannot follow the abrupt change in the direction of the flow, but they hit the collection surface 23a, 23b, being deposited on the same. When hitting the collection surface 23a, 23b, the charged particles cause a change in the charge level of the collection surface 23a, 23b. As the collection surface 23a, 23b is electrically coupled to said impactor stage 20a, 20 b which is, via an electrical coupling 27a, 27b further connected to a control u charge level of the collection surface 23a, 23b is indicated as an electric current which can be detected by sensitive current meters placed in the control unit 28.

The above-described method makes it possible to classify the particles selectively according to the size. By selecting, in a known way, the number and size of orifices in the nozzle part 22a, 22b, the distance between the nozzle part 22a, 22b and the collection surface 23a, 23b, as well as the flow rate to be used, each impactor stage 20a, 20b can be dimensioned so that only particles larger than a given particle size are deposited on the collection surface at each stage. By dimensioning successive impactor stages in such a way that particles with different particle sizes are collected on different stages, the currents from the different impactor stages 20a, 20b measured by the control unit 28 can be used to determine, in real time, the size distribution of the particles in the flow 11 to be measured, on the basis of the aerodynamic diameter.

As a result of the operating principle of the impactor, the impactors are most sensitive to particles whose mechanical mobility is small, i.e. typically particles with a large aerodynamic diameter. On the other hand, it is difficult to measure small particles with the impactors, because, due to the high mechanical mobility of the particles, high flow rates and abrupt changes in the direction of flow are thus required to separate the particles from the flow.

A problem with the above-presented real-time particle measurements of prior art has been their inapplicability for measurements in a wide range of particle sizes. DMA analyzers are suitable for the measurement of particles with a small diameter and high electric mobility, and impactors are suitable for the measurement of particles with a very large aerodynamic diameter.

In certain applications, it is advantageous to carry out the measurement of the particle size distribution within a wide range of particle sizes. If the measurement is made with an electric mobility analyzer, the problem is the poor sensitivity of the device for large particles, and if an impactor is used, the problem is the detection of small particles with a sufficient precision. Attempts have been made to solve this problem with prior art devices by carrying out the measurement in two parts, wherein an electric mobility analyzer 10 is first used to measure the size distribution of small particles. After this, the flow obtained from the mobility analyzer 10 through the outlet pipe 16 is guided to a separate impactor 20 to determine the size distribution of larger particles.

A problem in the above-described solution of prior art lies in the joint operation of the two separate measuring devices. Joint measurements with other measuring devices are typically not taken into account in the design of the measuring devices, wherein it is difficult to implement the centralized control of the different measuring devices. Furthermore, a problem may be presented by particle losses in the transfer pipe system between the different measuring devices.

SUMMARY OF THE INVENTION

It is an aim of the present invention to provide a novel device for the measurement of the size distribution of aerosol particles to overcome the above-presented problems of the solution of prior art. This is achieved by connecting an electric mobility analyzer and an impactor to each other in such a way that the bottom plate of the mobility analyzer is simultaneously used as the nozzle part of the first stage of the impactor.

BRIEF DESCRIPTION OF THE DRAWINGS

In the following, the invention will be described in detail with reference to the appended drawings, in which.

Figure 1:
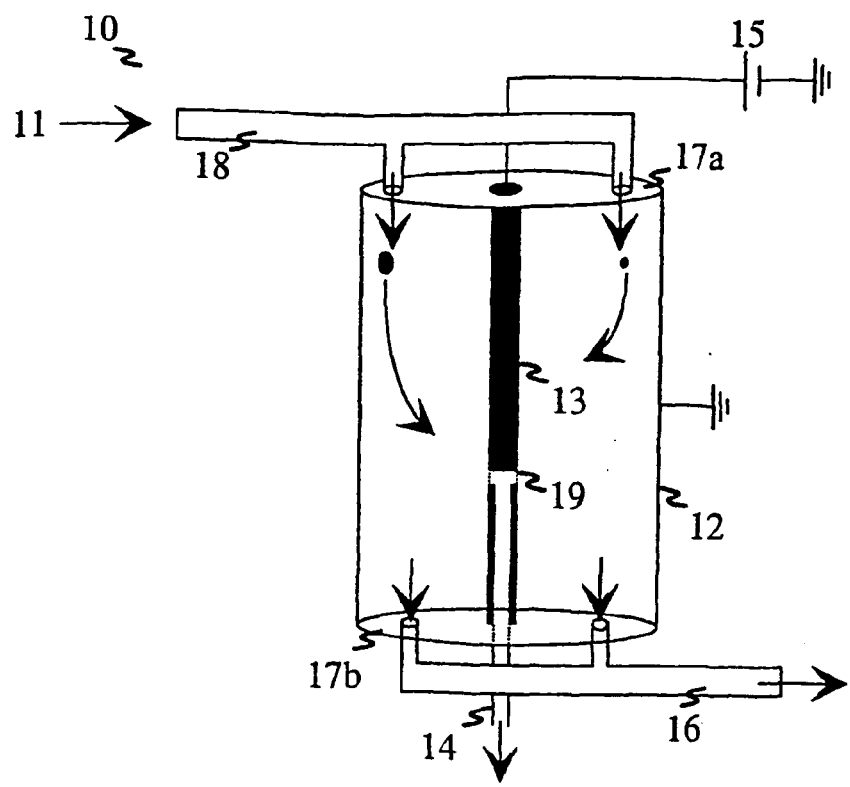
FIG. 1 shows an electric mobility analyzer according to prior art.
Figure 2:
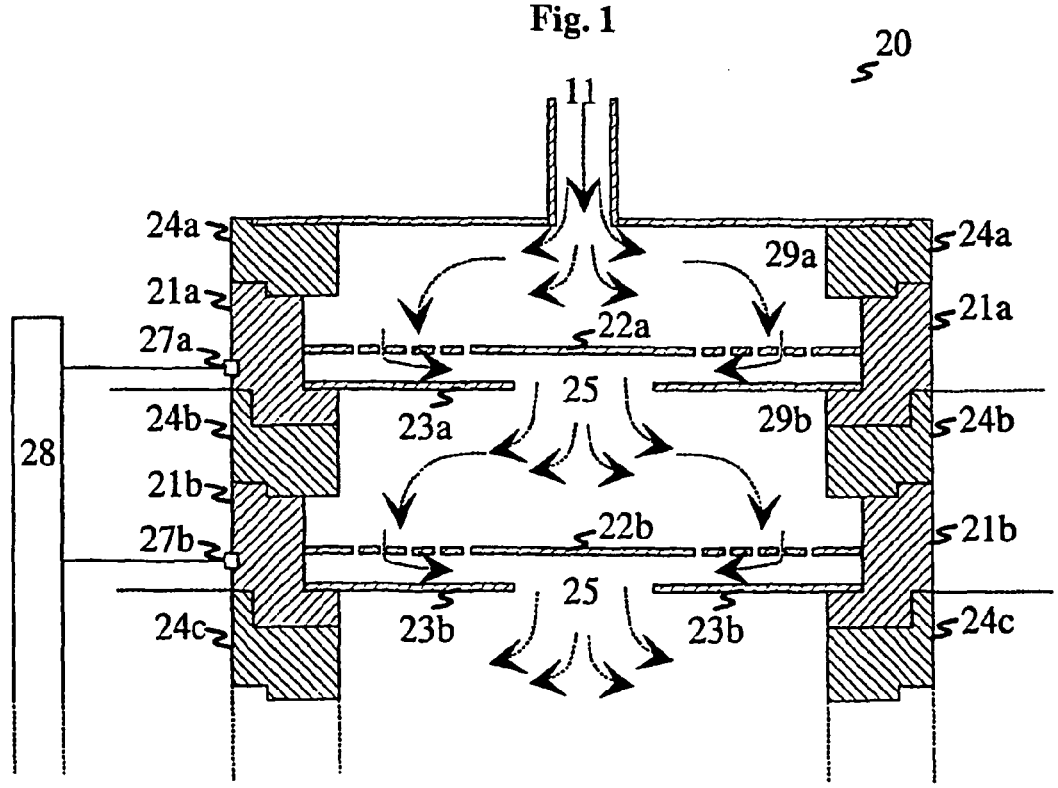
FIG. 2 shows an electric impactor according to prior art.

DETAILED DESCRIPTION OF THE PREFERRED EMBODIMENTS FIGS. 1 and 2 have been discussed above in connection with the description of prior art.

Figure 3:
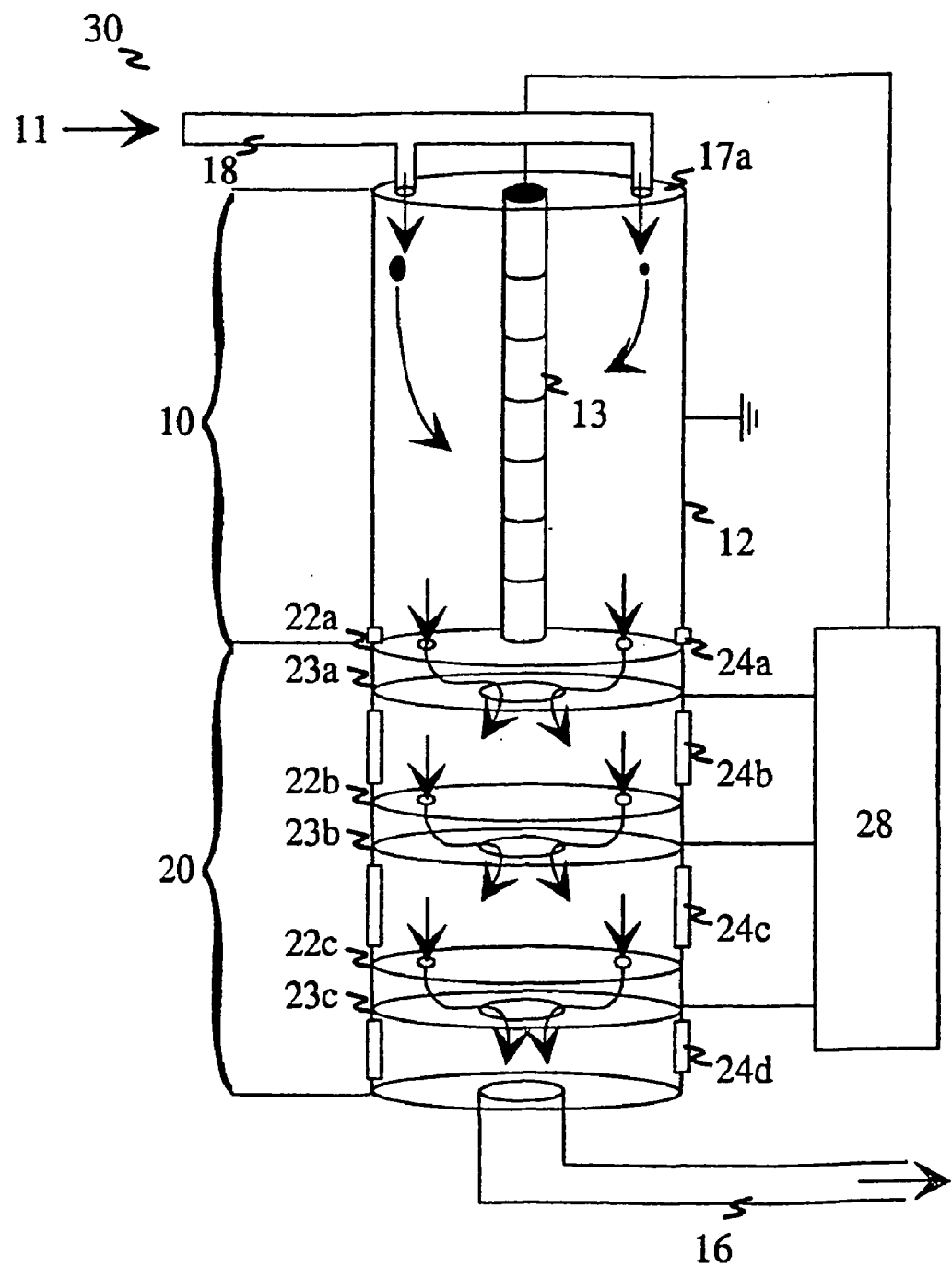
FIG. 3 shows a measuring device according to the invention.

FIG. 3 shows a device 30 for measuring the size distributions of aerosol particles according to the invention. The device 30 combines a mobility analyzer 10 and an impactor 20 into one device. As described above in connection with the operation of the mobility analyzer, the solution of the invention introduces a flow 11 to be analyzed via an inlet pipe 18 into the mobility analyzer 10. In the above-described manner, particles with a given electric mobility hit the inner electrode 13 of the mobility analyzer 10.

FIG. 3 shows a solution based on the above-mentioned multi-channel mobility analyzer, in which the inner electrode 13 of the mobility analyzer 10 is equipped with several measuring surfaces. However, the solution of the invention is not limited solely to said analyzer solution, but the mobility analyzer belonging to the device 30 according to the invention can also be implemented in another way, for example with a solution similar to that shown in FIG. 1, in which particles falling into a given mobility range are guided through a slit 19 into a second outlet pipe 14, the main flow 11 continuing its travel past the opening 19.

In the device 30 shown in FIG. 3, the flow passed through the mobility analyzer 10 is immediately guided into the impactor 20 coupled after the mobility analyzer 10. The coupling between the mobility analyzer 10 and the impactor 20 is preferably implemented so that the bottom plate 17b of the mobility analyzer 20, shown in FIG. 1, is the nozzle part 22a of the first stage of the impactor 20, shown in FIG. 2.

The impactor 20 of FIG. 3 comprises three stages 23a, 23b and 23c which are electrically separated by means of insulators 24a, 24b, 24c, 24d from each other and from the mobility analyzer 10.

The presented solution makes it possible to merge the mobility analyzer 10 and the impactor 20 into one compact analysis device 30. For example, the devices to be used for the control and calibration of the devices, such as the means required for adjusting the voltages of the mobility analyzer 10, can be centrally placed in a single control unit 28. Furthermore, the mobility analyzer 10 and the impactor 20 being clearly integrated in a single unit, the devices can be easily designed to support each other from the beginning, wherein the calibration and control of the integrated device can be implemented in a considerably simpler way than in the case of two separate measuring devices.

The mobility analyzer 10 and the impactor 20 can be advantageously designed in such a way that the mobility analyzer 10 is used to measure particles smaller than a given mobility-size distribution value, and the impactor 20 is used to measure particles larger than a given aerodynamic diameter value. The above-mentioned values can be preferably determined so that the mobility analyzer measures within the particle size range where it is more accurate than the impactor, and the impactor measures within a particle size range where it has a better measurement accuracy than the mobility analyzer. Naturally, the measurement ranges may also be partially overlapping.

Thanks to the solution of the invention, possible losses in the transfer pipe between the devices are also eliminated, which increases the reliability of the measurement, compared with the solution of two separate analyzers placed one after the other.

The solution of the invention is particularly well suitable for measurements of size distribution in real time, but it is not, however, solely limited to this solution, because the solution of the invention is also applicable in so-called integrating measurements (laittaisin näin vaikka vaikka alkutekstissälukeekin "mittaukseen"), in which particles to be measured are deposited in the analyzer for a certain period of time. After depositing the particles, the particles accumulated during the whole measurement period are measured.

The solution according to the invention is not limited solely to the above-described examples, but it may vary within the scope of the invention. In particular, the invention is not limited to the mobility analyzer and impactor types used in the examples, but the solution of the invention can be implemented with various mobility analyzer and impactor types, known as such.

Naturally, it will be obvious for anyone skilled in the art that the term "bottom plate" of the mobility analyzer, when used in the description and in the appended claims, generally refers to that part of the mobility analyzer through which the flow exits the analyzer. Said term should not be interpreted in a limited sense in such a way that it would always be the lowermost part of the mobility analyzer. If necessary, the bottom part may also comprise a design different from the plate-like shape, and protruding parts, etc., to implement the device of the invention.

The invention claimed is:

1. A device for determining the size distribution of aerosol particles from a flow, comprising:
   an electric mobility analyzer operative to receive the flow; and
   an impactor comprising a first stage including a nozzle part, wherein the impactor is operative to receive the flow from the electric mobility analyzer and is operatively connected to the mobility analyzer in such a way that the nozzle part of the first stage of the impactor also forms a bottom plate of said mobility analyzer, and said mobility analyzer and said impactor are designed so that said mobility analyzer collects from the flow particles smaller than a given mobility diameter value, and said impactor collects from the flow particles larger than a given aerodynamic diameter value, and wherein said mobility diameter value is such that said mobility analyzer operates on a particle size range where a measurement accuracy of said mobility analyzer is better than a measurement accuracy of said impactor and wherein said impactor measures particles within a particle size range where the impactor has a better measurement accuracy that the mobility analyzer.

2. The device according to claim 1, wherein said impactor is an electrical low pressure impactor.

3. The device according to claim 1, wherein said mobility analyzer is a multi-channel differential mobility analyzer.

4. The device according to claim 1, wherein substantially a whole flow passing through said mobility analyzer, excluding aerosol particles deposited in the mobility analyzer, is guided through the nozzle part of the first stage of the impactor.

5. The device according to claim 1, wherein said mobility diameter value and said aerodynamic diameter value correspond to the same particle size.

6. A device for determining the size distribution of aerosol particles from a flow to be analyzed, comprising:
   an electric mobility analyzer including an inlet for the flow; and
   an impactor comprising a first stage including a nozzle part including a guide operative to guide the flow from the mobility analyzer to the impactor, wherein the impactor is operatively connected to the mobility analyzer in such a way that the nozzle part of the first stage of the impactor also forms a bottom plate of said mobility analyzer, and said mobility analyzer and said impactor are designed so that said mobility analyzer collects particles smaller than a given mobility diameter value, and said impactor collects particles larger than a given aerodynamic diameter value, and wherein said mobility diameter value is such that said mobility analyzer operates on a particle size range where a measurement accuracy of said mobility analyzer is better than a measurement accuracy of said impactor and wherein said impactor measures particles within a particle size range where the impactor has a better measurement accuracy that the mobility analyzer.

7. The device according to claim 1, wherein said aerodynamic diameter value is such that said impactor operates on a particle size range where the measurement accuracy of said impactor is better than the measurement accuracy of said mobility analyzer.

8. The device according to claim 7, wherein said particle ranges where said impactor and said mobility analyzer operate are partially overlapping.

* * * * *